United States Patent

Stern

(10) Patent No.: US 6,724,189 B2
(45) Date of Patent: Apr. 20, 2004

(54) NUCLEAR DECAY LASER AND METHOD

(76) Inventor: Henry J. Stern, 12825 Buckland St., West Palm Beach, FL (US) 33414

( * ) Notice: Subject to any disclaimer, the term of this patent is extended or adjusted under 35 U.S.C. 154(b) by 101 days.

(21) Appl. No.: 10/025,053

(22) Filed: Dec. 18, 2001

(65) Prior Publication Data

US 2002/0093333 A1 Jul. 18, 2002

Related U.S. Application Data

(62) Division of application No. 09/303,480, filed on Apr. 30, 1999, now Pat. No. 6,331,774.

(51) Int. Cl.$^7$ .................................................. G01N 3/00
(52) U.S. Cl. ........................ 324/300; 324/307; 600/407
(58) Field of Search ................................ 324/300, 306, 324/307, 309, 312, 314, 318, 322; 600/407, 410, 416, 421, 422, 425

(56) References Cited

U.S. PATENT DOCUMENTS

| | | | |
|---|---|---|---|
| 4,576,777 A | 3/1986 | Weber | 376/153 |
| 4,641,095 A | 2/1987 | Riederer | 324/309 |
| 5,079,469 A * | 1/1992 | Bongianni | 310/301 |
| 5,280,428 A | 1/1994 | Wu et al. | 364/413.13 |
| 5,338,687 A | 8/1994 | Lee et al. | 436/173 |
| 5,617,859 A | 4/1997 | Souza et al. | 128/653.2 |
| 5,642,625 A | 7/1997 | Cates, Jr. et al. | 62/55.5 |
| 6,331,774 B1 * | 12/2001 | Stern | 324/300 |

* cited by examiner

*Primary Examiner*—Louis Arana
(74) *Attorney, Agent, or Firm*—Ryndak & Suri

(57) ABSTRACT

A nuclear decay laser that produces a stream of nuclear decay particles and/or photons of electromagnetic radiation. The stream of nuclear decay particles and/or photons is produced by subjecting radioactive materials to an external magnetic field which causes the radioactive nuclei to align with and precess around the external magnetic field vector. The precessing radioactive nuclei are then subjected to Radio Frequency (RF) pulses tuned to the Larmor frequency of the precessing nuclei which causes the nuclei to flip out of the plane of the external magnetic field vector into the X-Y plane. A refocusing RF pulse is then applied to the radioactive material which brings all of the magnetic moments of the flipped radioactive nuclei into phase. This can also be achieved with MRI gradient echo technology. When the initial RF pulse is discontinued, the flipped radioactive nuclei undergo T1 or spin-lattice relaxation which occurs when the radioactive nuclei relax back into phase with the external magnetic field vector during the process of T1 relaxation. The radioactive nuclei undergo accelerated coordinated decay with emission of a laser type pulse of electromagnetic radiation or particles according to the decay scheme of the radioactive nucleus. Alternatively, a ray of energy and/or particles is released when radioactive nuclei capable of undergoing fission experience a coordinated, accelerated fission reaction achieved when the refocusing RF pulse or gradient echo brings the radioactive nuclei into a coherent phase. The release of energy and/or particles can be focused and used in medical treatment and imaging, industrial and military applications, and for the production of energy. In addition, these methods of accelerating nuclear decay can be used to treat unwanted radioactive materials to background radiation levels providing for a way of disposing of unwanted nuclear waste.

9 Claims, 4 Drawing Sheets

NUCLEAR DECAY LASER AND METHOD

CROSS REFERENCE TO RELATED APPLICATION

This is a division of patent application Ser. No. 09/303,480, filed Apr. 30, 1999, now U.S. Pat. No. 6,331,774 B1.

BACKGROUND OF THE INVENTION a. Field of the Invention

The present invention generally relates to laser devices and methods and more specifically to laser devices and methods used in medical imaging, diagnostics and treatment, various industrial applications such as etching, military applications, and is also useful for treatment of nuclear waste and energy production.

b. Description of Related Art

Laser technology has experienced widespread acceptance and has been put to numerous uses in many aspects of everyday life. Lasers have found their way into the medical industry and their use is expanding rapidly. Lasers are also used in industrial applications such as etching, welding and the like. Similarly, with the intense energy output that lasers provide, there has also been interest in military applications and uses of lasers. Despite the state of laser technology there is a need for new and improved laser technology. Moreover, conventional laser technology, although useful, has proven inefficient, requiring much higher amounts of energy to achieve the laser effect which has often proven impracticable.

With the unlocking of atomic secrets and the advent of nuclear technology, humanity has received many benefits. However, through the use of nuclear technology problems have arisen that even advancing technology has been incapable of handling, namely how to deal with the radioactive waste created through the nuclear process. Currently, nuclear waste is essentially put into storage until the radioactive waste can be moved to a more proper location or the radioactivity lessens to background levels. Both pose a multitude of problems. In the first instance, to date there have been few promising ways of safely locking nuclear waste in a form that does not degrade and contaminate the environment. One technology for the safe storage of nuclear waste is a process called vitrification which essentially locks the waste into glassy medium which is then stored in containers. However, this process is extremely expensive and the long-term stability of such waste is unknown. Likewise, although governments have spent billions of dollars in a search for a suitable permanent nuclear waste repository the efforts so far have been fruitless. Other methods of treating nuclear waste have been proposed but none has proven to be sufficiently cost effective and safe to meet the ever-increasing demand to deal with nuclear waste.

Thus there is a need to effectively, safely and cost-effectively dispose of nuclear waste.

SUMMARY OF THE INVENTION

In accordance with one aspect of the present invention, a laser useful for medical imaging, diagnostics and treatment and associated methods are provided. In accordance with another aspect of the present invention, a laser useful for industrial applications such as etching and associated methods are provided. In accordance with another aspect of the present invention, a laser suitable for military applications is provided. In accordance with still another aspect of the present invention, a treatment system and method for nuclear waste through coordinated, spontaneous accelerated decay of radioactive nuclei is provided. In accordance with a related aspect of this invention, the release of the nuclear decay laser to produce another form of energy, such as electricity, is provided.

In accordance with the invention, a nuclear decay laser device is provided. The nuclear decay laser device in accordance with the invention includes at least a radioactive element, a magnetic field source associated with the radioactive element for generating and subjecting the radioactive element to a magnetic field external to the radioactive element. A source of radio frequency energy is provided for subjecting the radioactive element to a radio frequency energy tuned to the Larmor frequency of the precessing radioactive nuclei of sufficient intensity to flip the radioactive nuclei to a flip angle sufficient to allow the radioactive nuclei to release energy in the form of electromagnetic radiation and/or particles upon relaxation of the radioactive nuclei caused by termination of the radio frequency energy.

In accordance with another aspect of the invention, a nuclear decay laser imaging device, suitable for medical imaging and other imaging purposes is provided. The nuclear decay laser imaging device in accordance with the invention comprises at least one radioactive element, a magnetic field source associated with the radioactive element for generating and subjecting the radioactive element to a magnetic field external to the radioactive element. A source of radio frequency energy is provided for subjecting the radioactive element to a radio frequency energy tuned to the Larmor frequency of the precessing radioactive nuclei of sufficient intensity to flip the radioactive nuclei to a flip angle sufficient to allow the radioactive nuclei to release energy in the form of electromagnetic radiation and/or particles upon relaxation of the radioactive nuclei caused by termination of the radio frequency energy. A specimen area is provided for placing matter to be imaged by the released energy and detecting structure is provided for detecting the interaction of the released energy with the matter placed in the specimen area. Any suitable detection or imaging structure can be utilized, such as X-ray film, a CT scanner or a suitable electronic detecting device, for example.

In accordance with another aspect of the present invention, a method for the treatment of nuclear waste composed of a radioactive element is provided. The method includes the steps of placing the nuclear waste in the magnetic field external to the nuclear waste, subjecting the nuclear waste to a radio-frequency wave tuned to the Larmor frequency of the precessing radioactive nuclei of the radioactive element, providing the radio-frequency pulse with sufficient strength and duration to flip the radioactive nuclei such that the relaxation of the radioactive nuclei will release energy in the form of heat, electromagnetic radiation and/or particles. The flipped radioactive nuclei are allowed to relax thereby releasing their energy and accelerating the rate of decay of the radioactive nuclei relative to the normal rate of decay of said nuclei.

In accordance with another aspect of the present invention, a method for producing electrical energy from nuclear waste is provided. The method includes the steps of placing the nuclear waste in the magnetic field external to the nuclear waste and subjecting the nuclear waste to a radio-frequency wave tuned to the Larmor frequency of the precessing radioactive nuclei of the nuclear waste. The radio-frequency pulse is provided with sufficient strength and duration to flip the radioactive nuclei such that the relaxation of the radioactive nuclei will release energy in the form of heat, electromagnetic radiation and/or particles. The flipped radioactive nuclei are allowed to relax thereby releasing their energy. A structure is provided for absorbing the released energy to directly or indirectly produce electric current.

In one embodiment, at least one type of radioactive material which possesses an angular momentum and magnetic moment is encompassed within a cylindrical magnet, preferably of at least 1 Tesla, wherein the center of the magnet has been removed along the lengthwise axis of the magnet to accommodate placement of the radioactive material within the magnet. As is typical with conventional MRI devices, the cylindrical magnetic core is surrounded by an outer cryoshield and inner magnetic windings. Homogeneity of the magnetic field can be achieved through shim coils, for example. Gradient recall pulse sequences are generated by gradient coils. The radioactive specimen is surrounded by a cylindrical transmit-receive radio-frequency (RF) coil such that the open end of the RF coil is directed along the axis of the magnet defined by the direction of the main magnetic field $B_o$.

When the radioactive nuclei are placed in the external magnetic field $B_o$, the nuclei precess about the external magnetic field vector $B_o$. The frequency of this precession is defined by the Larmor equation. The RF coil is tuned to the Larmor frequency of the radioactive nuclei placed in the magnetic field to produce an RF pulse having a frequency that is matched to the Larmor frequency of the precessing nuclei. This is accomplished using the Larmor equation:

$$\omega = \gamma \cdot B_o$$

where $\omega$ is the frequency of nuclear precession about the main external magnetic field vector $B_o$;

$\gamma$ is the gyromagnetic ratio; and $B_o$ is the strength of the magnetic field (in Tesla)

Matching the RF pulse to the Larmor frequency of the radioactive nuclei placed in the magnetic field results in absorption of energy by the radioactive nuclei which causes the nuclei to assume a flip angle, which is defined as the degree to which the nucleus tips toward the X-Y plane and is dependent upon the magnitude and duration of the RF pulse. A flip angle of 90° results in revolution of the radioactive nucleus in the X-Y plane.

Upon termination of the RF pulse, T1 spin-lattice relaxation of the radioactive nuclei occurs. The process of T1 spin-lattice relaxation occurs when the nuclei resume their relaxed state along the Z axis ($B_o$ vector). During this relaxation process, the radioactive nuclei undergo coordinated, spontaneous decay and generate energy, which can be in the form of heat electromagnetic radiation and/or radioactive particles, according to the natural decay scheme of the radioactive material, which is a laser as that term is used herein, released along the Z axis or the magnetic field vector. The application of the RF pulse and subsequent energy release in the form of heat, electromagnetic energy and/or particle release through T1 relaxation can be repeated until the radioactive material has undergone complete radioactive decay or decay to a desired level.

In accordance with the invention, a laser beam or emission is also produced by rephasing of the nuclei in the X-Y plane to correct for T2 spin-spin relaxation. Loss of coherence of the nuclei is prevented by applying a 180° refocusing RF pulse to the nuclei as in spin-echo MRI imaging where the 180° refocusing pulse generates the echo. T2 relaxation may also be corrected by performance of MRI gradient echo technology. Loss of coherence of the nuclei in the X-Y plane is effectively prevented by applying the refocusing pulse very shortly after termination of 90° RF pulse, by either spin-echo or gradient echo refocusing technology.

In accordance with another aspect of the invention, laser energy, either in the form of electromagnetic radiation and/or particles, can be released when nuclear materials that are capable of undergoing fission are flipped into the X-Y plane and a 180° refocusing pulse or gradient echo pulse is applied thereby causing the radioactive nuclei to reach critical mass in which electromagnetic energy and/or particles are spontaneously released by accelerating and coordinating nuclear fission of these materials.

DETAILED DESCRIPTION OF THE INVENTION

Figure 1:
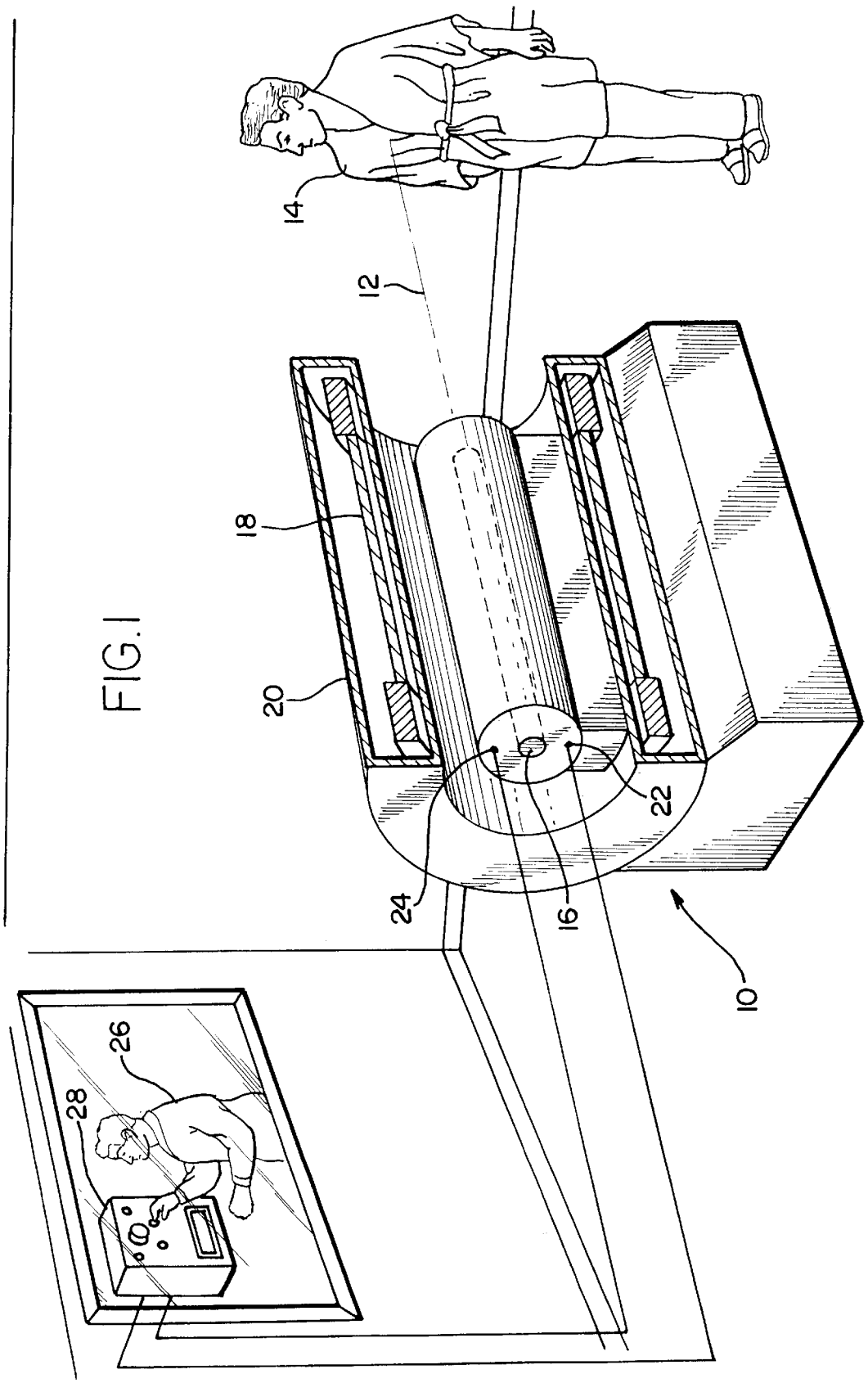
FIG. 1 is a perspective view of the present invention wherein the device is being used for medical purposes.

Referring first to FIG. 1, in accordance with the present invention, a nuclear decay laser 10 is shown producing a beam, stream or ray 12 of energy and/or particles which is being used to treat a subject 14, represented here as a patient. Nuclear decay laser 10 consists of radioactive material 16 placed approximately within the center of a conventional MRI device consisting of a cylindrical magnet 18, preferably of at least 1 Tesla, which produces a magnetic field vector $B_o$ and is encased in a magnet housing 20, radio-frequency (RF) coil 22, and cylindrical magnetic field gradient coils 24. The stronger the external magnetic field the greater will be the nuclear decay laser pulse. Nuclear decay laser 10 produces the stream of energy and/or particles 12 through manipulation of the nuclei of the radioactive material 16 by the cylindrical magnet 18, RF coil 22, and cylindrical magnetic field gradient coils 24 all under the direction of an operator 26 acting through a control panel 28. Nuclear decay laser 10 is shown in the treatment of subject 14. This treatment may include, but is not limited to radiation therapy, diagnostic purposes, and medical imaging wherein the resultant interaction of the beam 12 with the subject 14 can be detected and imaged by a suitable device, such as through X-ray film, CT scanner or a suitable electronic detecting array, for example.

In order to more clearly describe the production of stream 12, the operation of the device as shown in FIG. 1 will be discussed in conjunction with FIGS. 2–9 which graphically represent manipulation of the radioactive nuclei. In FIGS. 2–9, N is a vector representation of the nuclei of radioactive material 16 shown in FIG. 1. Nuclear vector N is depicted in a three dimensional graphical environment conventionally represented by X, Y and Z axes. The Z axis is defined as the external magnetic field $B_o$ vector produced by cylindrical magnet 18.

Figure 2:
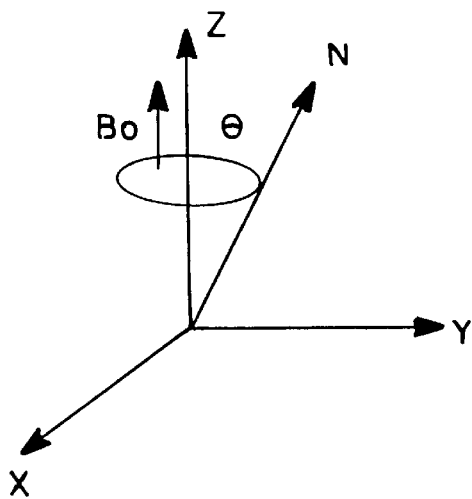
FIG. 2 is a graphical representation of the magnetic moment of nuclei precessing around the external magnetic field vector which is aligned parallel to the z-axis ($B_o$)

Nuclear vector N of radioactive material 16 possessing a magnetic moment will align along, and precess around, the external magnetic field vector $B_o$ or Z axis as represented in FIG. 2. The frequency of nuclear precession is the Larmor frequency. The radio-frequency (RF) coil 22 is tuned to the Larmor frequency of the radioactive nuclei N using the Larmor equation ($\omega=\gamma \cdot B_o$). For example, $\gamma$ for technetium 99 m is 9.5808781 Mhz/Tesla; $\gamma$ for U 235 is 0.76635 Mhz/Tesla; and $\gamma$ for tritium is 45.412125 Mhz/Tesla.

Figure 3:
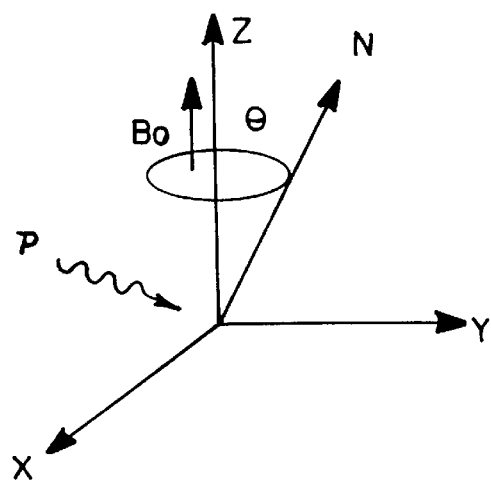
FIG. 3 is a graphical representation of the nuclei precessing around the external magnetic field vector being subjected to a RF pulse tuned to the Larmor frequency of the nuclei.

To initiate the production of beam 12 technician 26 prompts the appropriately tuned RF coil 22 to emit an RF pulse P, the frequency of which is matched to the Larmor frequency of the precessing nuclei. This matched RF pulse is absorbed by the precessing nuclei N as is shown in FIG. 3.

Figure 4:
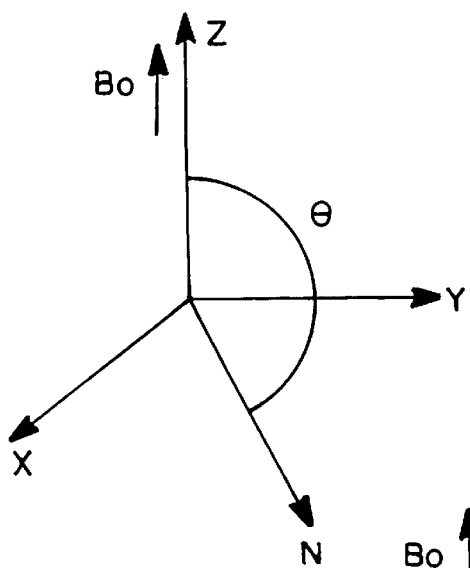
FIG. 4 is a graphical representation of the nuclei flipped 90° into the X-Y plane after being subjected to the RF pulse shown in FIG. 3.

Absorption of the RF pulse by the nuclei N results in the nuclei N tipping away from the external magnetic field vector $B_o$. The degree to which the nuclei N flip out of the external magnetic field vector $B_o$ is referred to as the flip angle $\theta$ and is dependent upon the strength and duration of the RF pulse. A flip angle $\theta$ of 90° results in nuclei revolving in the X-Y plane. This absorption of the tuned RF pulse P by nuclei N in FIG. 3 resulting in a flip angle $\theta$ of 90° and subsequent revolution of the nuclei N in the X-Y plane is depicted in FIG. 4.

Figure 5:
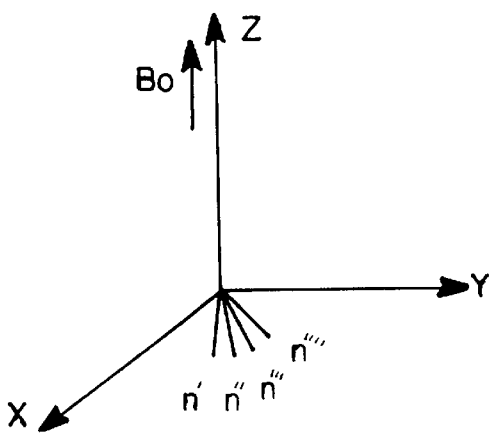
FIG. 5 is a graphical representation of the flipped nuclei in FIG. 4 spontaneously dephasing in the X-Y plane (T2 relaxation)

Once nuclear vector N has been flipped into the X-Y plane the nuclei spontaneously lose coherence into individual nucleus n', individual nucleus n", individual nucleus n'" and individual nucleus n"" by T2 or spin-spin relaxation as depicted in FIG. 5.

Figure 6:
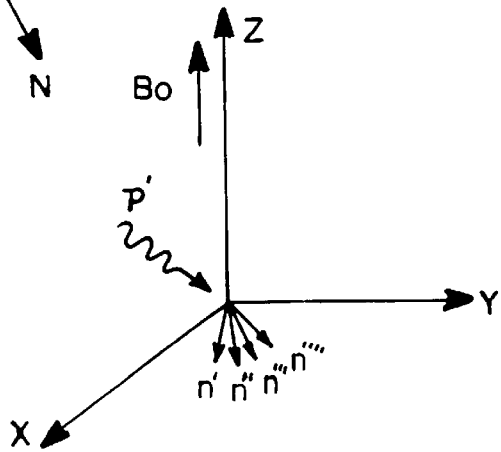
FIG. 6 is a graphical representation of the dephased nuclei shown in FIG. 5 being subjected to a 180° refocusing pulse.

To restore the coherence of individual nucleus n', individual nucleus n", individual nucleus n'" and individual nucleus n"" the conventional MRI device of the nuclear decay laser 10 is prompted by either the operator 26 or through automatic programming of the MRI device to apply a 180° refocusing RF pulse P' which is absorbed by individual nucleus n', individual nucleus n", individual nucleus n'" and individual nucleus n"" as shown in FIG. 6. The 180° refocusing pulse can be performed through conventional MRI spin echo techniques. Nuclear coherence can also be achieved by conventional MRI gradient echo techniques.

Figure 7:
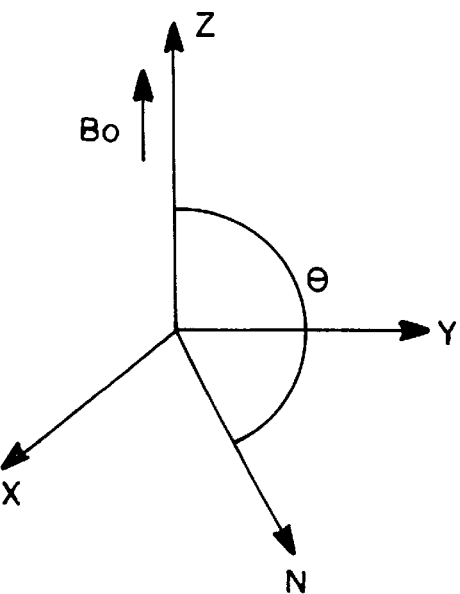
FIG. 7 is a graphical representation of the nuclei shown in FIG. 6 rephased in the X-Y plane after the nuclei have been subjected to the 180° or gradient echo refocusing pulse.
Figure 8:
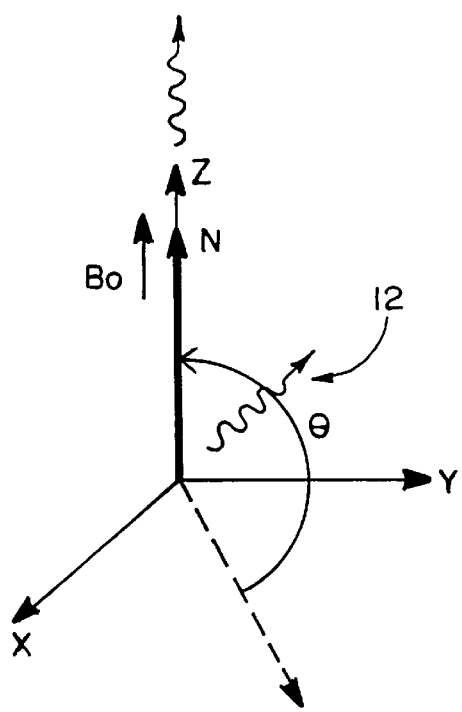
FIG. 8 is a graphical representation of the rephased nuclei shown in FIG. 7 relaxing back into alignment with the external magnetic field vector along the Z axis.

This absorption of the 180° refocusing pulse or gradient echo technology results in coherent nuclei N revolving in the X-Y plane as depicted in FIG. 7. Preferably, to ensure minimal nuclear dephasing and loss of coherence the 180° refocusing pulse P' or gradient echo should be applied as shortly after RF pulse P is terminated as practicable.

Upon termination of RF pulse P and the 180° refocusing pulse P' or gradient echo the nuclear vector N will spontaneously relax back into alignment with the Z axis or external magnetic field vector $B_o$. This is termed T1 relaxation. As part of T1 relaxation the radioactive nuclei will undergo accelerated spontaneous coordinated nuclear decay with emission of a laser type beam 12 of electromagnetic radiation and/or subatomic particles in accordance with the nuclear decay scheme of the nuclear material placed in the nuclear decay laser.

Figure 9:
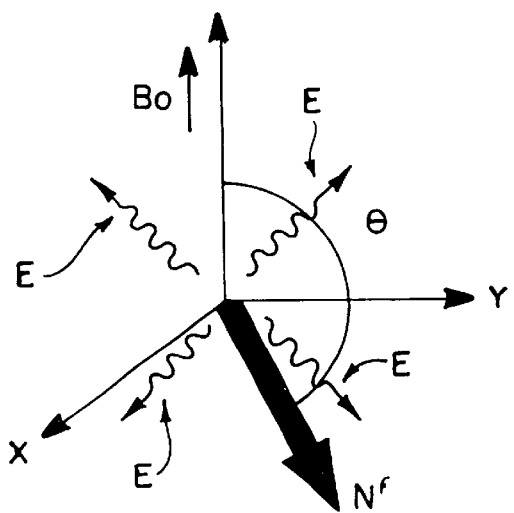
FIG. 9 is a graphical representation of fissionable nuclei that have been rephased as in FIG. 7 undergoing coordinated fission.

FIG. 9 depicts an alternative method of producing a release of energy and/or particles E wherein radioactive material 16 consists of fissionable nuclei $N^f$ that is flipped into the X-Y plane and is subjected to a 180° refocusing pulse P' or gradient echo so that the fissionable nuclei $N^f$ reaches a critical mass resulting in the release of energy and/or particles. In the preferred embodiment, RF pulse P would be terminated shortly before the application of the 180° refocusing RF pulse P' or gradient echo, however, there may be instances where it is desirable to subject the fissionable nuclei $N^f$ to the RF pulse P and the 180° refocusing RF pulse P' concurrently to achieve a prolonged state of critical mass resulting in energy and/or particle release. As defined herein, critical mass is the state of fissionable nuclei $N^f$ experienced when a coordinated, accelerated fission reaction is achieved after the 180° refocusing RF pulse P' or gradient echo brings the fissionable nuclei N into a coherent phase in the X-Y plane.

Figure 10:
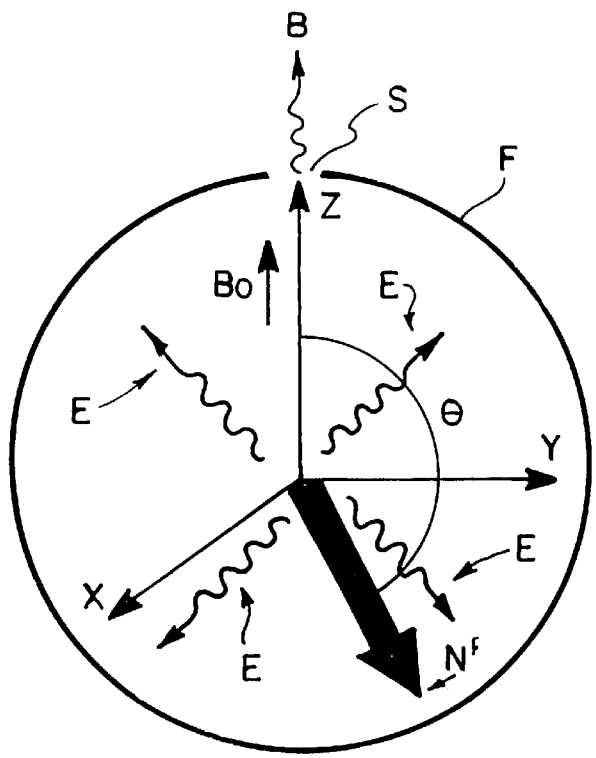
FIG. 10 is a graphical representation of the focusing of energy and/or particles released from fissionable nuclei undergoing coordinated fission as in FIG. 7.

FIG. 10 depicts the focusing of the release of energy and/or particles as shown in FIG. 9 being focused into a beam, ray or stream B, similar to stream 12, through the use of a focusing element F. Focusing element F is depicted as a sphere or other enclosure of material capable of shielding the environment external to the fissionable nuclei $N^f$ from the release of energy and/or particles provided with a slit S which facilitates the release of the beam B in a controlled manner. Focusing of the beam B may also be provided through other focusing means including electromagnetic or chromatic focusing.

Figure 11:
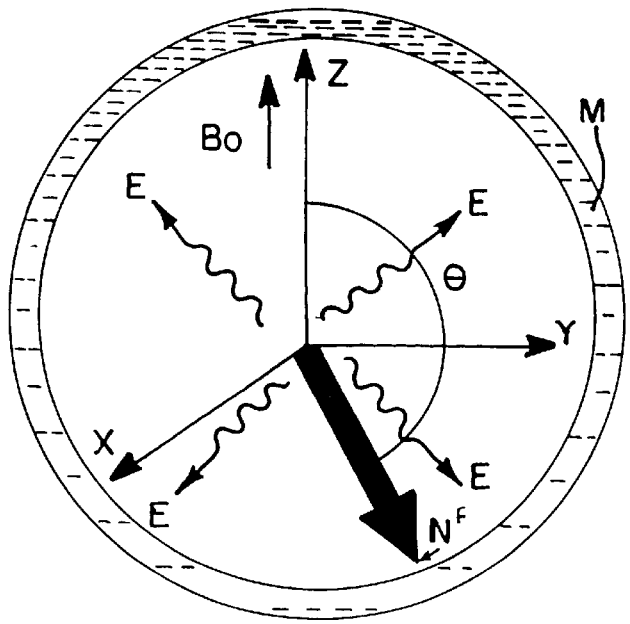
FIG. 11 is a graphical representation of the harnessing of energy and/or particles released from fissionable nuclei undergoing coordinated fission as in FIG. 7 to produce energy.

FIG. 11 depicts the release of energy and/or particles E depicted in FIG. 9 being absorbed and transferred to a medium M which is then used to produce energy in another form, such as electricity, by well-known methods. Conventionally, energy production is achieved through the heating of water which, through phase changes and thermal force, drives turbines which, in turn, drive generators to produce electricity.

It will be understood that the invention is capable of numerous changes, modifications and rearrangements and such changes, modifications and rearrangements are intended to be within the scope of the following claims.

What is claimed is:

1. A method for the treatment of nuclear waste composed of a radioactive element comprising the steps of:
   (a) placing the nuclear waste in a magnetic field external to the nuclear waste;
   (b) subjecting the nuclear waste to a radio-frequency wave tuned to the Larmor frequency of the precessing radioactive nuclei of the radioactive element;
   (c) providing the radio-frequency pulse with sufficient strength and duration to flip the radioactive nuclei such that relaxation of the radioactive nuclei will release energy in the form of heat, electromagnetic radiation and/or particles;
   (d) allowing the flipped radioactive nuclei to relax thereby releasing said energy and accelerating the decay of the radioactive nuclei relative to the normal rate of decay of said nuclei.

2. The method of claim 1 wherein the external magnetic field is at least 1 Tesla.

3. The method of claim 1 wherein the flip angle achieved is 90° or greater.

4. The method of claim 1 wherein the flipped radioactive nuclei are subjected to a refocusing pulse to bring the nuclei into coherency before the nuclei decay releasing energy and/or particles.

5. The method of claim 1 further comprising producing an electric current from the released energy.

6. The method of claim 5 wherein said producing an electric current comprises heating water with the released energy from the radioactive waste.

7. A method for production of electrical energy from nuclear waste composed of a radioactive element comprising the steps of:

(a) placing the nuclear waste in a magnetic field external to the nuclear waste;

(b) subjecting the nuclear waste to a radio-frequency wave tuned to the Larmor frequency of the precessing radioactive nuclei of the nuclear waste;

(c) providing the radio-frequency pulse with sufficient strength and duration to flip the radioactive nuclei such that relaxation of the radioactive nuclei will release energy in the form of heat, electromagnetic radiation and/or particles;

(d) allowing the flipped radioactive nuclei to relax thereby releasing said energy; and (e) means for absorbing the released energy to directly or indirectly produce electric current.

8. The method of claim 7 wherein said means for absorbing the released energy from the radioactive waste comprises heating water.

9. The method of claim 8 wherein said means for absorbing the released energy from the radioactive waste to produce electric current comprises driving a turbine by the heated water.

* * * * *